United States Patent [19]

Higham

[11] 4,350,037

[45] Sep. 21, 1982

[54] PERSONAL GAS MONITOR

[75] Inventor: Peter Higham, High Wycombe, England

[73] Assignee: Perkin-Elmer Limited, England

[21] Appl. No.: 213,249

[22] Filed: Dec. 5, 1980

[30] Foreign Application Priority Data

Jul. 12, 1979 [GB] United Kingdom ............... 7942327

[51] Int. Cl.³ .......................... G01N 1/22; G01N 7/04
[52] U.S. Cl. .................................. 73/23; 73/863.21; 422/88
[58] Field of Search ................. 73/863.21, 23; 422/88; 55/270

[56] References Cited

U.S. PATENT DOCUMENTS

| | | | |
|---|---|---|---|
| 3,950,980 | 4/1976 | Braun et al. | 73/23 |
| 3,985,017 | 10/1976 | Goldsmith | 73/23 |
| 4,040,805 | 8/1977 | Nelms et al. | 73/23 |
| 4,158,958 | 6/1979 | Braun | 73/23 |
| 4,235,097 | 11/1980 | Kring | 73/23 |
| 4,267,023 | 5/1981 | Frant | 73/23 |

Primary Examiner—S. Clement Swisher
Attorney, Agent, or Firm—S. A. Giarratana; F. L. Masselle; R. A. Hays

[57] ABSTRACT

A column of particulate adsorbent is located within a longitudinally extending stainless steel tube. The pollutant gas to be monitored reaches the adsorbent by molecular diffusion after passing through a diffusion gauze at the diffusion end of the tube, a stagnant diffusion zone and a partition gauze forming one longitudinal boundary of the column. In one embodiment the diffusion gauze is removably mounted in a diffusion cap that may be slid over the tube; in another, the diffusion gauze and the partition gauze are mounted in a unit which in manufacture is fitted and permanently fixed within the tube. The invention establishes that the repeatability problem in molecular diffusion personal monitors lies in the hitherto unsuspected criticality of the stagnant diffusion zone parameters and provides a general solution enabling a good compromise between repeatability and sensitivity without the need for unduly close manufacturing tolerances.

36 Claims, 9 Drawing Figures

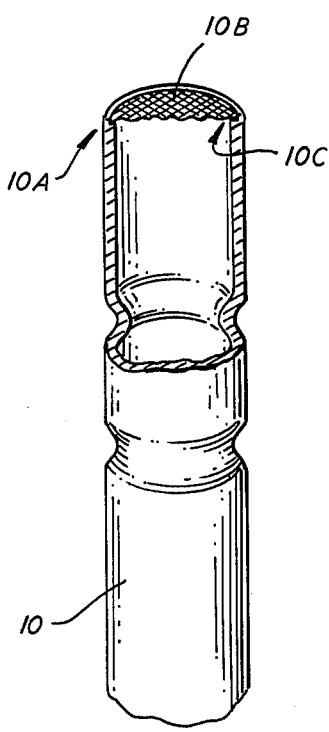
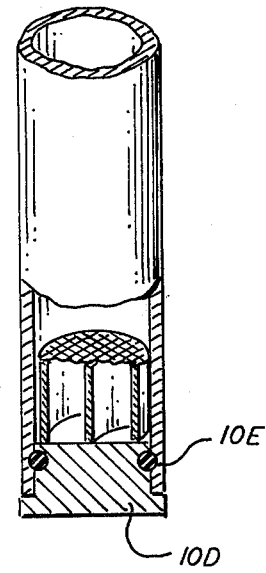
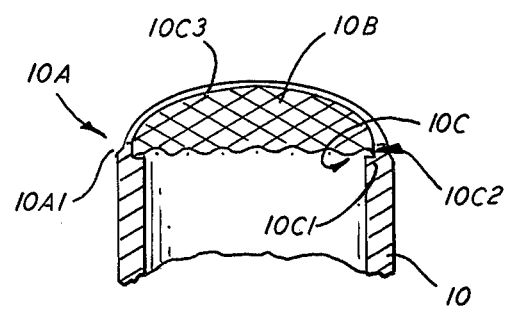
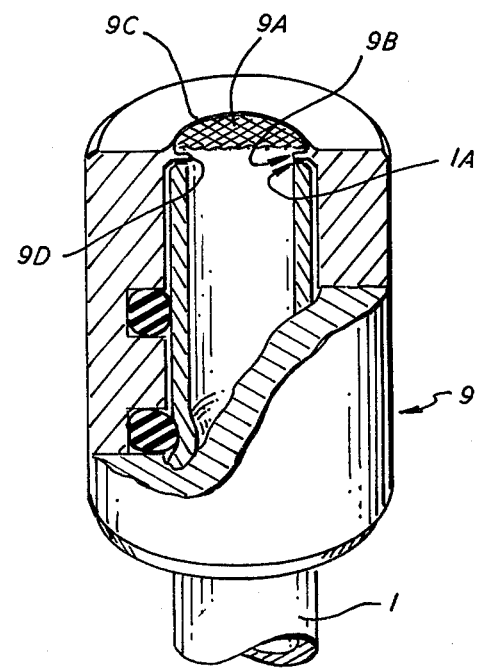
FIG. 6
FIG. 5
FIG. 4

PERSONAL GAS MONITOR

BACKGROUND OF THE INVENTION

This invention generally relates to personal gas monitors intended to be worn on the person of anyone likely to be exposed to an atmosphere polluted with noxious gases in concentrations ranging from a fraction to several hundred ppm (parts per million), as typically found in certain industrial situations, and in particular to longitudinally extending personal gas monitors (hereinafter also referred to as personal monitors) containing a column of adsorbent to which the pollutant gains access by molecular diffusion during the period the personal monitor is actually in use and from which it may be thermally desorbed and analyzed later in order to establish the total exposure suffered by the wearer over the said period.

Ideally, a personal monitor must be so constructed as to ensure high repeatability of results, in the sense that the total exposure evaluated by analysis should only be a function of the concentration of the adsorbed gas at the end of a given exposure period. It is largely with a view to securing good repeatability that known personal gas monitor tubes are normally associated with a small vacuum pump for aspiring the polluted atmosphere through a suitable adsorbent, which occupies most of the tube inner volume. The pump is driven by an electric motor powered by a battery. In the present state of the art, pumped tubes systems may be regarded as being generally satisfactory, but they are expensive, comparatively bulky and, therefore, inconvenient in use; above all, they need to be calibrated quite frequently since there are many variable factors, including mechanical wear, that can affect the pumping efficiency and, therefore, the volume of polluted air aspired during a given period. For these reasons non-reusable personal monitor badges relying on molecular diffusion of the pollutant through the adsorbent are in much more common use in all but the most exacting situations.

A badge-type personal monitor is usually constructed in a synthetic resin and may comprise injection moulded parts which snap together. It is comparatively cheap, therefore. In addition, it requires no ancillaries of any kind and contains no moving parts.

Despite claims to the contrary, badge-type personal monitors do not in general provide outstanding repeatability. This may be due partly to the manner of their construction, which does not allow sufficiently narrow tolerances to be maintained, and partly to the undue emphasis placed on sensitivity when the requirements of high sensitivity (and therefore high molecular diffusion rate) and repeatability are largely incompatible. This latter point requires amplification.

It is by now well established that in order to provide good repeatability the rate of diffusion should not be significantly affected by the velocity of the air movement over the diffusion aperture through which the polluted atmosphere gains access to the adsorbent within. It is known that the provision of a stagnant diffusion zone between the said aperture and the free surface of the adsorbent is essential to securing comparative insensitivity to air current. In this the assumption is made that the adsorbent is so efficient that at the free surface thereof the concentration of the pollutant is near zero, and that, therefore, a molecular diffusion gradient tends to be set up in the diffusion zone that essentially varies only in response to concentration changes of the pollutant in the atmosphere. Assuming the personal monitor to be generally cylindrical, the approximation to this desirable condition becomes closer the greater the length of the diffusion zone compared with its average diameter. A factor close to 2 is very desirable. This is not achieved by the badge monitors. In fact, the badges in common use either provide no diffusion zone at all or at best a shallow one. At all events, the length of the zone is not even as great as its average diameter (or, in the case of either circular or non-circular cross-section, its average breadth). If badges were constructed for optimum repeatability, they would have to be unacceptably protruberant when attached to the wearer's clothing. The inadequacy of the diffusion zone is to some extent alleviated in certain designs by the provision of a membrane pervious to the pollutant for the purpose of creating a stagnant barrier layer co-operating with the stagnant atmosphere in the diffusion zone. These designs appear to improve matters in some respects but their repeatability still leaves a lot to be desired, particularly in the monitoring of gas so noxious that only a concentration of a fraction of 1 ppm can be tolerated in an eight-hour exposure period.

Apart from indifferent repeatability, there is another drawback associated with the badges: the adsorbent therein can only be desorbed in the solvent mode-the temperature associated with the alternative thermal desorption mode would cause the badges to collapse. This could be overcome by constructing the badges in a suitable material but then their shape would be unsuitable and would make them quite expensive if realized in a material such as stainless steel, which stands up to the desorption temperature and is comparatively inert.

Solvent desorption involves a comparatively simple manual operation but is much less suited to automation than the thermal desorption mode. In addition, the solvent commonly used is carbon disulphide, which being toxic and very highly inflammable may be more objectionable than the pollutant to be monitored. Having particular regard to the growing concern for the health of industrial workers, likely to result in the passing of legislation compelling employers to carry out mass monitoring of certain categories of workers, the time may soon be here when only an automated system for handling, desorbing and analysing the samples collected through personal monitors will be a practical proposition in large industrial organizations employing thousands of workers potentially exposed to varying concentrations of noxious gases.

It was at first believed that non-pumped molecular diffusion tubes would almost inevitably provide better repeatability compared with badge monitors, since it is so much easier to provide a stagnant diffusion zone having the desired characteristics for repeatability within a longitudinally extending hollow member rather than a shallow vessel. When batches of tubes constructed along conventional lines, which essentially involved locating a column of granular adsorbent between two glass-wool plugs, leaving however a generous air space between the open end of the tube acting as the diffusion aperture and the free surface of the facing glass-wool plug, it was found that repeatability was no better than could be achieved with some known badge monitors. This unexpected finding seemed to suggest that, although the importance of providing an adequate diffusion zone ahead of the adsorbent had been generally appreciated, some unidentified problem stood in the way of obtaining superior repeatability.

In the present context, personal monitors of a given design provide good repeatability if after a statistically significant batch (say, 50) of such monitors has been exposed to a standard polluted atmosphere, desorbed and analyzed, in accordance with a strictly controlled procedure, they yield pollutant concentrations in which the standard deviation is within limits that are tolerable for the chosen pollutant.

SUMMARY OF THE INVENTION

In view of the foregoing, one object of the present invention is to identify the problem which has hitherto prevented molecular diffusion personal monitor tubes from achieving a repeatability close to that of properly calibrated pumped tubes and to solve the problem in the context of molecular diffusion personal monitor tubes suitable for thermal desorption.

In attempting to identify the problem referred to, it was observed that even when a permeable membrane of the kind used in some known badge monitors was stretched over the diffusion aperture of each molecular diffusion tube used in the experiment referred to earlier, repeatability was still not as good as might have been reasonably predicted, which seemed to suggest at first that there was nothing wrong with the diffusion zone as arranged; but when the glass-wool plug above the adsorbent was replaced with a substantially incompressible semirigid perforate partition member provided with openings small enough to prevent the adsorbent granules from passing therethrough, a substantial improvement was immediately detected. This led to the permeable membrane itself being advantageously replaced with a similar perforate member. The repeatability problem was beginning to take shape; clearly it was not enough to provide a sufficiently elongated molecular diffusion zone (without unacceptable sacrifice of sensitivity, of course) and to create a boundary layer of stagnant gas at the diffusion aperture, the actual geometry of the diffusion zone had to be maintained with unsuspected accuracy, which could not be achieved in nominally identical tubes using such dimensionally unstable devices as a glass-wool plug and an inadequately supported permeable membrane at the boundary of the diffusion zone. It was later found that not only the spacing between the two perforate members had to be maintained within close tolerances but also the effective inner diameter of the tube itself. All this posed a production problem since the tolerances would have to be chosen so as not to impair repeatability even in a worst case situation, i.e. inner diameter of the tube near positive limit and perforate members spacing near negative limit in certain tubes and the inverse in other tubes of, say, the same batch. Fortunately, it was found that provided the diffusion zone had a length that was no less than twice its average breadth and said average was no less than about 3 mm a compromise could be reached between unacceptably tight tolerances and low sensitivity in achieving high repeatability.

In accordance with the present invention there is provided a molecular-diffusion personal gas-monitor suitable for thermal desorption of the gases that in use will be adsorbed in a particulate adsorbent within the monitor, comprising:

(a) a longitudinally extending hollow body into which gases may diffuse by molecular diffusion via one end thereof representing the diffusion end and through which gases may be back-flushed following thermal desorption;

(b) a low-compressibility partition pervious to said gases but not to the adsorbent, said partition being located in a predetermined longitudinal axial position within the hollow body so as to present a free surface that faces the diffusion end at a predetermined distance therefrom;

(c) means including the said partition for retaining a column of adsorbent within the hollow body, with one end of the column abutting against the surface of the partition opposite said free surface, and (d) a diffusion screen at the diffusion end in predetermined spaced relation to the partition so as to define a stagnant diffusion zone of predetermined volume therebetween, the spacing being no less than about twice the average breadth of the diffusion zone measured at right angles to the longitudinal axis of the hollow body and said average breadth being no less than 3 mm.

The diffusion screen may be removably retained in a diffusion cap slidable over the hollow body, from the diffusion end thereof, and provided with abutment means co-operating with the hollow body to predetermine the spacing between the diffusion screen and the partition. Alternatively, the diffusion screen may be fixedly retained in the diffusion cap in such manner that no material stands substantially proud of the diffusion screen face exposed to the atmosphere. In the same manner the diffusion screen may be fixed into the hollow body itself at the diffusion end thereof.

The partition may be retained within the hollow body with the co-operation of means integral with the hollow body (e.g. swaged parts) or means forming part of a separately manufactured insert (e.g. locating annulus forced into hollow body). In addition to locating the partition within the hollow body the insert may be made to maintain an accurately predetermined spacing between the diffusion screen and the partition.

The construction may advantageously ensure that the average breadth of the diffusion zone is between 3 mm and 13 mm, but preferably between 4 mm and 6 mm.

Specific embodiments of the present invention will now be described by way of examples, with reference to the accompanying diagrammatic drawings.

BRIEF DESCRIPTION OF THE DRAWINGS

FIG. 4 is a modification of the diffusion cap 6 of FIG. 1.

FIG. 5 is a longitudinal partly cross-sectional view of another personal gas monitor in accordance with the invention.

FIG. 6 is an enlarged cross-sectional view of the diffusion end of the FIG. 5 personal gas monitor.

DETAILED DESCRIPTION OF THE INVENTION

Figure 1:
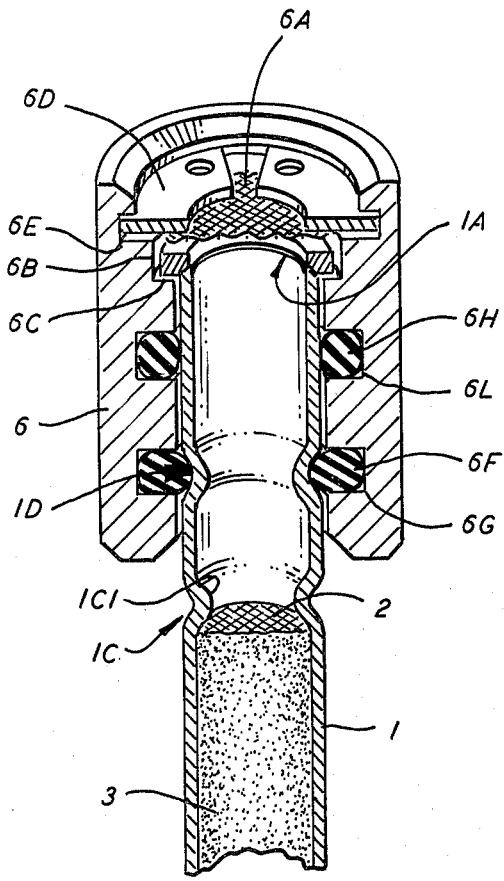
FIG. 1 is a longitudinal cross-sectional view of a personal gas monitor in accordance with the invention.

The personal gas monitor depicted in FIG. 1 comprises a longitudinally extending hollow body in the form of a stainless steel tube 1 of substantially circular cross-section having a length of 89 mm, an outer diameter of 6.35 mm and an inner diameter of 5 mm. Tube end 1A represents the diffusion end, through which a gas to be monitored gains access by molecular diffusion and the gas adsorbed within the tube may be desorbed to a suitable analytical instrument, e.g. gas chromatograph, by thermal desorption, a carrier gas being fed through the tube end 1B to sweep the monitored gas into the instrument.

A disc-like stainless steel gauze 2, of approximately 100 mesh and 0.5 mm average thickness, fitting tightly against the wall of tube 1 and abutting against an inward annular projection 1Cl resulting from forming a constriction 1C in said wall, represents a rigidly fixed low-compressibility partition pervious to said gas. The upper surface of the partition gauze 2 is spaced 15 mm from the inner edge of the chamfered diffusion end 1A. Proper tooling design ensures that the spacing is accurately maintained in manufacture.

A column 3 of a particulate adsorbent abuts against the lower surface of the partition gauze 2 and is prevented from falling out by an end gauze 4, which unlike the partition gauze 2 is made a loose fit in the tube 1 and is held in position by an S-spring 5 bearing against the wall of tube 1. This provision enables the adsorbent to be changed at will after withdrawing the spring 5 with a pair of long nosed pliers and allowing the gauze 4 to fall out. The column 3 is therefore held between retaining means represented by partition gauze 2 and end gauze 4, the mesh size of both gauzes being such as to prevent the adsorbent from passing therethrough.

Different kinds of adsorbent may of course be used to make up the column 3, depending on the nature of the gases to be monitored.

A generally cylindrical diffusion cap 6 is provided which is slid onto the tube 1 from the diffusion end 1A just before the personal monitor is put into use. At the trailing end of diffusion cap 6, a diffusion screen in the form of diffusion gauze 6A is located within a recess 6B, between a backing annulus 6C and a circlip 6D fitting into a groove 6E. The arrangement is such that some compression must be applied on circlip 6D before it may be sprung radially into the groove 6E. In this manner the gauze 6A is firmly and accurately located axially of the diffusion cap 6, with no trace of play.

A leading O-ring 6F, accommodated in groove 6G, co-operates with the constriction 1D in tube 1 in establishing a detent action when the diffusion cap 6 is about to reach the end of its travel, the inner diameter of the O-ring 6F as fitted in the groove 6G being smaller than the outer diameter of the tube 1, so that, when the diffusion cap 6 is slid over the tube 1, the O-ring 6F must deform slightly, until it relaxes into the upper portion of the arcuate constriction 1D and thus generates a force component which tends to bring the diffusion cap 6 into deeper engagement with the tube 1. This force is resisted by the abutment of the diffusion end 1A against the annulus 6C before the diffusion cap 6 has moved far enough for the O-ring 6F to relax completely into the constriction 1D. Thus the O-ring 6F is kept under a shear stress (as indicated in FIG. 1) which ensures that the abutting parts referred to are biased towards each other.

The volume included between the partition gauze 2 and the diffusion screen 6A represents the all-important stagnant diffusion zone. The detent action and the abutment action together ensure that the predetermined volume of the stagnant diffusion zone is accurately defined when the diffusion cap is fully home. In addition, the abutment reacts against the upper face of the groove 6E via the circlip 6D and the intervening diffusion screen 6A, which means that any undue force used in fitting the cap is prevented from causing a deformation of the screen 6A capable of affecting the length of the stagnant diffusion zone.

In addition to the leading O-ring 6F the diffusion cap 6 is provided with a trailing O-ring 6H accommodated in the groove 6L. The function of O-ring 6H is to form a reliable gas seal between the diffusion cap 6 and the co-operating outer surface of tube 1, to ensure that the gases to be monitored can only diffuse through the tube 1 via the diffusion gauze 6A. The leading O-ring 6F will itself provide some sealing action, of course, but since it will be largely relaxed at the end of the cap travel, the action may not be entirely reliable without the back up of the trailing O-ring 6H. O-rings 6F and 6G are both made of fluorinated rubber.

Figure 2:
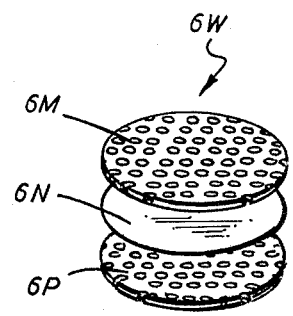
FIG. 2 is a porous membrane assembly for optional use with the monitor of FIG. 1.

In certain personal monitoring situations encountered in practice, it may be desirable to fit a permeable membrane acting as a diffusion screen. In fitting the membrane care should be taken to ensure that the effective height of the stagnant diffusion zone is not made uncertain by the use of an essentially flimsy material that can be easily deformed. A suitable arrangement is depicted in FIG. 2, which shows, in exploded view, a thin wafer generally inclined at 6W comprising a silicone rubber membrane 6N well supported between foraminous discs 6M and 6P. The wafer 6W may be fitted under slight compression (which incidentally will impede relative rotation of parts) between annulus 6C (FIG. 1) and circlip 6D in place of the diffusion gauze 6A, with the perforations in disc 6M carefully aligned with those in disc 6P. To assist alignment, a pair of registration marks may be provided, one in each disc.

The foraminous discs may be produced by photo-etching or chemical milling techniques in order to minimize as much as possible dimensional variations due to the manufacturing process. In fact, the diffusion gauze 6A and the partition gauze 2 may themselves be substituted with similar discs.

Mounting the diffusion gauze 6A in the removable diffusion cap 6, rather than fixedly in the tube 1, means that a gas tight connection with the diffusion end 1A, as required for the thermal desorption operation, may be made without the encumbrance of the said diffusion gauze 6A and fear of damaging it, the diffusion cap 6 being of course removed before the operation.

At the desorption end 1B, the tube 1 is provided with a blanking cap 7 having a sealing O-ring 7A in groove 7B for providing a gas seal between the blanking cap 7 and the tube 1. The blanking cap 7 must of course be fitted when the personal monitor is being worn and removed before thermal desorption is carried out. When the personal monitor is in transit or storage before or after use, the blanking cap 7 must also be fitted and a similar cap must cover the diffusion end 1A.

Figure 3:
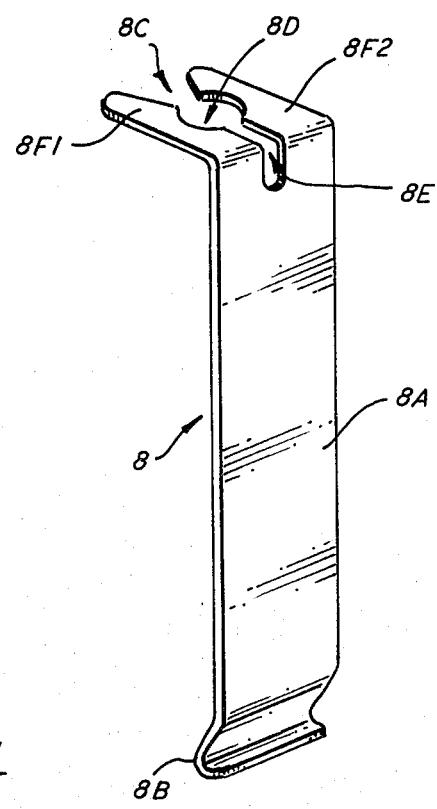
FIG. 3 is a pocket clip for attachment to any of the personal gas monitors depicted in FIGS. 1, 5 and 7, respectively.

The personal monitor as shown in FIG. 1 is ready for use, but to facilitate its attachment to the wearer's clothes in a vertical attitude (which is recommended), a clip in the fashion of a pen clip may be provided. The clip generally indicated at 8 in FIG. 3 is particularly convenient, since it may be sprung into the existing groove 1C of tube 1 (FIG. 1). The clip 8 is generally L-shaped, with the short limb uppermost as shown. The long limb comprises a comparatively extensive flat area 8A, which can be used for labelling purposes, and terminates in a re-entrant part forming a rearward projection 8B, similar to that found in regular pen clips for providing a good grip on fabric. The short limb is provided with a V-slot indicated at 8C extending into a circular aperture 8D leading to a springing cut 8E and thus forming two sprung arms 8F1 and 8F2. Referring to FIG. 1 and FIG. 3, the clip 8 may be fitted to the tube 1 by engaging the groove 1C with the V-slot 8C, forcing open the arms 8F1 and 8F2 and snapping the tube 1 into the circular aperture 8D.

Labelling of the personal monitor tube fitted with the clip of FIG. 3 may take different forms. One of the simpler ways is to attach a self-adhesive label to the labelling area 8A. Naturally, either the label must be resistent to the full thermal desorption temperature or provision must be included in the desorption apparatus to ensure that the label is suitably protected, e.g. by static heat sinking or air cooling. It has been found in practice that the problem is not a serious one. The desorption temperature is in any case limited to the maximum value that the adsorbent will stand and the clip itself is easily maintained well below that temperature, mainly by virtue of the comparatively high thermal impedance existing between the clip 7 and the tube 1 and the comparatively large surface area of the clip 7. If slidable labels are preferred, the basic design shown in FIG. 3 may be easily modified by striking out retaining lugs or forming channels. A separate label carrier sprung onto the long limb is another possibility.

A modification of the diffusion cap 6 shown in FIG. 1 is embodied in the diffusion cap 9 depicted in FIG. 4. It consists in permanently fixing a diffusion gauze 9A into a shallow annular recess 9B by swaging over the thin rim 9C (see also description of FIG. 6 relating to similar construction) or in any other way which avoids contamination of the parts, e.g. electron beam welding. In operation, the underside of the annular ledge 9D provides an abutment for the diffusion end 1A of the tube 1. The diffusion cap 9 is essentially a dedicated device but, on the other hand, it is simpler to construct and, more significantly, effectively presents no part that stands proud of the upper face of the diffusion gauze 9A (the swaged over rim 9C is practically co-planar with the said upper face), which tends to prevent the formation of an undesirable shallow stagnant or semi-stagnant zone ahead of the intended stagnant diffusion zone.

It was stated earlier that the provision of the removable diffusion cap facilitates connection of the thermal desorption apparatus to the diffusion end. In fact, when the modification of FIG. 3 is applied to the tube of the personal monitor, the diffusion cap may be eliminated altogether, with very little loss of operational convenience but a significant gain in terms of simplification of design and avoidance of a shallow stagnant zone. This is illustrated in FIG. 5, wherein 10 corresponds to tube 1 in FIG. 1, but with the diffusion end 10A (see also enlarged view in FIG. 6) modified to retain a diffusion gauze 10B in a recess 10C. Referring mainly to FIG. 6, the recess 10C is bounded by a shoulder portion 10C1, a cylindrical wall portion 10C2 and a rim portion 10C3. The diffusion gauze 10B is initially an easy fit in the recess 10C and becomes firmly fixed therein, but without distortion, after the rim 10C3 is carefully swaged over to establish a practically co-planar relationship between it and the upper face of the diffusion gauze 10B. In swaging over the rim 10C3, a small upper part of the cylindrical wall portion 10C2 will tend to collapse inwards thus holding the diffusion gauze 10B captive. The diffusion end 10A is chamfered at 10A1 and the rim 10C3 is finished flat after swaging for the purpose of permitting an easy temporary connection with the thermal desorption apparatus (not shown). At the other end of tube 10 a blanking plug 10D having a sealing O-ring 10E may be substituted for the blanking cap 7 of FIG. 1 in order to take full advantage of the slimness of design made possible by dispensing with the diffusion cap.

Figure 7:
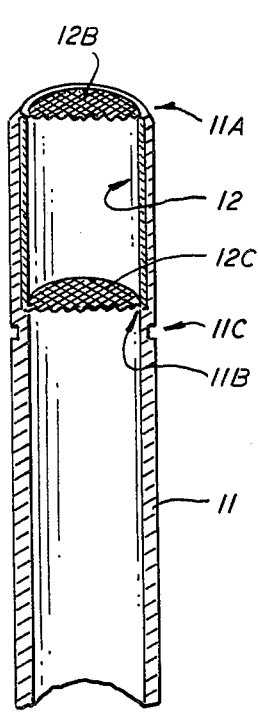
FIG. 7 is yet another personal gas monitor in accordance with the present invention.

FIG. 7 illustrates an embodiment in accordance with the present invention which represents a different balance of convenience in constructional and operational terms compared with the embodiment of FIG. 1. Not only the diffusion cap has been dispensed with but the critical parameters of the all-important diffusion zone have been fully predetermined in an insert unit constructed separately from the tube. The personal monitor of FIG. 7 comprises a tube 11 having an internal diameter of 5 mm bored out to 5.5 mm for a length of 15 mm from the diffusion end 11A so as to define a shoulder 11B. Forced into the bored out portion up to the shoulder 11B is a cylindrical insert unit 12 shown enlarged in FIG. 8, wherein the unit 12 comprises a stainless steel sleeve 12A fitted with a diffusion gauze 12B at the top end and a partition gauze 12C at the bottom end. The gauzes are fitted in symmetrical recesses generally indicated at 12D and 12E, respectively. The profile of each said recesses, when facing upward, and the manner in which a gauze is fitted therein are the same as described with reference to recess 10C retaining gauze 10B in FIG. 6. It may also be helpful to refer to FIG. 9, wherein parts 12D1, 12D2 and 12D3 correspond to 10C1, 10C2 and 10C3 in FIG. 6.

Figure 8:
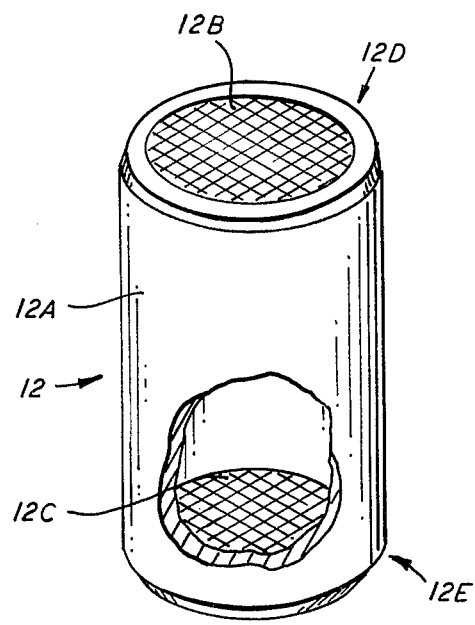
FIG. 8 is an insert unit forming part of the personal gas monitor of FIG. 7.
Figure 9:
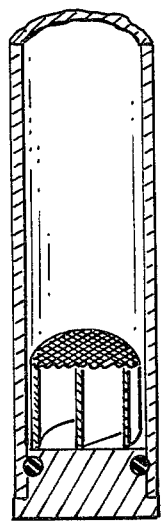
FIG. 9 is an enlarged cross-sectional view of the diffusion end of the FIG. 7 personal gas monitor.
Figure 9:
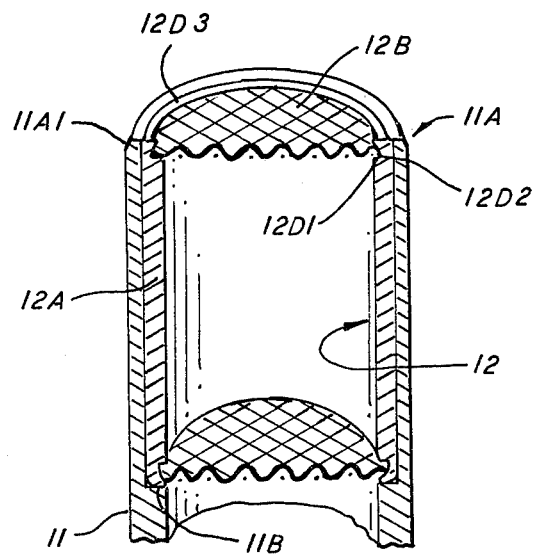

The actual termination of the tube 11 (FIG. 7) after the unit 12 (FIGS. 7 and 8) has been fitted into the bored out portion of tube 11 is shown enlarged in FIG. 9, wherein the parts are referenced as in FIGS. 7 and 8. In FIG. 9, the diffusion end 11A of the tube 11 has itself been swaged over towards the rim 12D3 of sleeve 12A, after which an external chamfer has been precision ground at 11A1 and the very end of the tube ground flat. The object of the construction is to produce a good gas tight connection between the sleeve 12A and the tube 11 and a tube termination which avoids a shallow stagnant zone while permitting a good temporary connection with the thermal desorption apparatus.

A groove 11C may be provided in the tube 11 (FIG. 7) for fitting therein the clip of FIG. 3, if so desired.

The embodiments and modifications described with reference to FIGS. 4 to 9 are particularly useful in situations where a fixed diffusion screen of a given mesh size is acceptable and the need to fit a porous membrane does not arise. If the diffusion screen need not be changed but a porous membrane is occasionally required, the devices described may be readily adapted to take a sleeve mounting a membrane the upper face of which abuts against a gauze which in co-operation with the diffusion gauze provides full support for the membrane similarly to the arrangement of FIG. 2.

The personal monitors of FIGS. 1, 1 and 4, 5 and 7, respectively, each embodies the identification and a practical solution of the repeatability problem within the ambit of the present invention. They achieve an excellent compromise between sensitivity and repeatability without imposing production tolerances that would be too tight to maintain in practice. For example, because of the chosen length of the stagnant diffusion zone in relation to its average breadth, it has not been found necessary to fine bore the tube 1 or the tube 10 in correspondence of said zone. If, in order to achieve the ultimate in repeatability, fine boring is called for, the embodiment of FIG. 7 is preferred since the separately produced unit 12 represents a very convenient workpiece to handle. The embodiment of FIG. 1 on the other hand will be found adequate in the vast majority of the situations encountered in practice. It offers the user a greater freedom in the selection of the diffusion screen and the porous membrane.

What is claimed is:

1. A molecular-diffusion personal gas monitor compatible with thermal desorption of the gases adsorbed within the monitor, comprising:- a longitudinally extending hollow body into which gases can diffuse by molecular diffusion via one end thereof representing the diffusion end and through which gases can be back-flushed following thermal desorption; a low-compressibility partition pervious to said gases but not to the adsorbent, said partition being located in a predetermined longitudinal axial position within the hollow body so as to present a free surface facing the diffusion end at a predetermined distance therefrom; means including the said partition for retaining a column of adsorbent within the hollow body, with one end of the column abutting against the surface of the partition opposite said free surface; and a diffusion screen at the diffusion end in predetermined spaced relation to the partition so as to define a stagnant diffusion zone of predetermined volume therebetween, the spacing being no less than about twice the average breadth of the diffusion zone measured at right angles to the longitudinal axis of the hollow body and said average breadth being no less than 3 mm.

2. A monitor as claimed in claim 1, wherein the average breadth of the stagnant diffusion zone is between 3 mm and 13 mm.

3. A monitor as claimed in claim 1, wherein the average breadth of the stagnant diffusion zone is between 4 mm and 6 mm.

4. A monitor as claimed in any one of claims 1, 2 and 3, wherein the diffusion screen is mounted in a diffusion cap slidable over the hollow body from the diffusion end thereof and provided with abutment means for co-operating with the hollow body in establishing said predetermined spaced relation between the diffusion screen and the partition.

5. A monitor as claimed in claim 4, wherein the diffusion screen is removable.

6. A monitor as claimed in claim 5, wherein the diffusion screen is retained in a groove within the diffusion cap by means of a clip.

7. A monitor as claimed in claim 4, wherein the diffusion cap is provided with a gas seal between the inner surface of the diffusion cap and the outer surface of the hollow body whereby gases can gain access to the hollow body through the diffusion screen only.

8. A monitor as claimed in claim 7, wherein the gas seal is an O-ring of fluorinated rubber.

9. A monitor as claimed in claim 4, wherein the hollow body is provided with an annular constriction and the diffusion cap is provided with a part for engaging the constriction and producing a detent action when the abutment means of the diffusion cap is about to engage the diffusion end of the hollow body whereby a force is generated that maintains the engagement.

10. A monitor as claimed in claim 4, wherein the diffusion screen is permanently fixed in the diffusion cap.

11. A monitor as claimed in claim 10, wherein the diffusion screen is located in a recess and firmly held therein by a swaged over part of the material in which the recess is formed.

12. A monitor as claimed in claim 10, wherein the diffusion screen is located in a recess and firmly held therein by a contamination-free weld between the screen and the material in which the recess is formed.

13. A monitor as claimed in claim 4, wherein the hollow body is provided with a gas-tight blanking cap at the end opposite the diffusion end.

14. A monitor as claimed in any one of claims 1, 2 and 3, wherein the diffusion screen is permanently fixed at the diffusion end of the hollow body.

15. A monitor as claimed in claim 14, wherein the diffusion screen is permanently attached to the wall of the hollow body.

16. A monitor as claimed in claim 15, wherein the diffusion screen is located in a recess at the diffusion end of the hollow body and firmly held therein by a swaged over part of the material in which the recess is formed.

17. A monitor as claimed in claim 15, wherein the diffusion screen is located in a recess at the diffusion end of the hollow body and firmly held therein by a weld between the screen and the material in which the recess is formed.

18. A monitor as claimed in claim 14, wherein the diffusion screen is permanently attached to an insert unit that is permanently fixed within the hollow body.

19. A monitor as claimed in claim 18, wherein the insert unit comprises a machined sleeve fixedly mounting the diffusion screen at one end and the partition at the other.

20. A monitor as claimed in claim 19, wherein the sleeve is provided with end recesses for accommodating therein the diffusion screen and the partition, respectively.

21. A monitor as claimed in claim 20, wherein the fixing of the diffusion screen and the partition within their respective recesses is provided by a swaged over portion of the material in which the recesses are formed.

22. A monitor as claimed in claim 20, wherein the diffusion screen and the partition are held within the recesses by a contamination-free welded joint.

23. A monitor as claimed in claim 19, wherein the hollow body has a bored out portion extending from the diffusion end into which fits the sleeve, the hollow body being swaged against the sleeve at the diffusion end to provide a gas tight connection therebetween.

24. A monitor as claimed in claim 14, wherein the hollow body is provided with a gas-tight blanking cap at the end opposite the diffusion end.

25. A monitor as claimed in claim 1, comprising means for locating the partition within the hollow body.

26. A monitor as claimed in claim 25, wherein the partition locating means is formed within the hollow body.

27. A monitor as claimed in claim 26, wherein the partition locating means is an inward annular projection formed by constricting the wall of the hollow body at a predetermined distance from the diffusion end.

28. A monitor as claimed in claim 25, wherein the partition locating means is formed by an insert that is permanently fixed within the hollow body.

29. A monitor as claimed in claim 1, wherein the hollow body is provided with an external groove for locating a clip therein in the fashion of a pen clip.

30. A monitor as claimed in claim 29, comprising a generally L-shaped clip the short limb of which is provided with two resilient arms for springing into said external groove and the long limb of which is in the shape of a flat extended strip the width of which is no less than the external diameter of the tube.

31. A monitor as claimed in claim 30, wherein one at least of said parts is a gauze.

32. A monitor as claimed in claim 30, wherein one at least of said parts is a smooth perforated disc.

33. A monitor as claimed in claim 1, wherein the diffusion screen and the partition are each a stainless steel part.

34. A monitor as claimed in claim 1, wherein the hollow body is a length of stainless steel tube of substantially circular cross section having a chamfer at the diffusion end.

35. A monitor as claimed in claim 34, wherein the stagnant diffusion zone is defined within a fine bored wall.

36. A monitor as claimed in claim 34, wherein the means for retaining a column of adsorbent within the hollow body include a member axially spaced from the partition and, like the partition, pervious to gases but not to the adsorbent, the monitor further including a column of adsorbent between the partition and the said member.

* * * * *